(12) United States Patent
Traynor et al.

(10) Patent No.: US 8,974,709 B2
(45) Date of Patent: *Mar. 10, 2015

(54) CERAMIC ENCAPSULATION WITH CONTROLLED LAYERING BY USE OF PREHYDROLYZED FUNCTIONALIZED SILANES

(75) Inventors: Daniel H. Traynor, Sarasota, FL (US); Hao Xu, Canton, MI (US); Henry G. Traynor, Sarasota, FL (US); Daniel H. Traynor, legal representative, Sarasota, FL (US); John Carson, Union City, NJ (US); Martin S. Flacks, Danville, CA (US); Rachel Sullivan, Addison, TX (US)

(73) Assignee: CoLabs Intl Corp, Las Vegas, NV (US)

( * ) Notice: Subject to any disclaimer, the term of this patent is extended or adjusted under 35 U.S.C. 154(b) by 282 days.

This patent is subject to a terminal disclaimer.

(21) Appl. No.: 13/168,730

(22) Filed: Jun. 24, 2011

(65) Prior Publication Data

US 2012/0104639 A1 May 3, 2012

Related U.S. Application Data

(60) Provisional application No. 61/358,737, filed on Jun. 25, 2010.

(51) Int. Cl.

| *B01J 13/22* | (2006.01) |
| *B29B 9/12* | (2006.01) |
| *B01J 13/18* | (2006.01) |
| *A01N 25/28* | (2006.01) |
| *A61K 8/02* | (2006.01) |
| *A61K 8/25* | (2006.01) |
| *A61Q 5/02* | (2006.01) |
| *A61Q 11/00* | (2006.01) |
| *A61Q 17/04* | (2006.01) |
| *A61Q 19/00* | (2006.01) |
| *C01B 33/18* | (2006.01) |
| *C11D 3/50* | (2006.01) |
| *C11D 17/00* | (2006.01) |
| *A61K 47/02* | (2006.01) |
| *A61K 9/00* | (2006.01) |

(52) U.S. Cl.
CPC ............ *B01J 13/18* (2013.01); *A01N 25/28* (2013.01); *A61K 8/0279* (2013.01); *A61K 8/25* (2013.01); *A61Q 5/02* (2013.01); *A61Q 11/00* (2013.01); *A61Q 17/04* (2013.01); *A61Q 19/00* (2013.01); *B01J 13/22* (2013.01); *C01B 33/18* (2013.01); *C11D 3/505* (2013.01); *C11D 17/0039* (2013.01); *A61K 47/02* (2013.01); *A61K 9/0092* (2013.01); *A61K 2800/412* (2013.01); *A61K 2800/413* (2013.01); *C01P 2004/34* (2013.01)
USPC ......... 264/4.32; 427/212; 427/213.3; 264/4.1

(58) Field of Classification Search
USPC ......... 428/321.5, 402–402.24, 403, 404, 407, 428/331, 389.9, 212, 213.3–213.36, 483, 428/256; 427/534, 41, 4–4.7; 424/59, 60, 424/63, 400, 408, 450, 451, 455, 93.7, 424/184.1, 497, 489, 501, 490, 491, 492, 424/493, 494, 495; 623/16.11; 510/158, 510/106
See application file for complete search history.

(56) References Cited

U.S. PATENT DOCUMENTS

| 5,126,061 | A | 6/1992 | Michael |
| 5,387,622 | A | 2/1995 | Yamamoto |
| 6,251,313 | B1 | 6/2001 | Deubzer et al. |
| 6,468,509 | B2 | 10/2002 | Lapidot et al. |
| 6,855,335 | B2 | 2/2005 | Seok et al. |
| 6,998,113 | B1 | 2/2006 | Traynor et al. |
| 7,001,592 | B1 | 2/2006 | Traynor et al. |
| 7,025,952 | B1 | 4/2006 | Traynor et al. |
| 7,037,513 | B1 | 5/2006 | Traynor et al. |
| 7,153,525 | B1 | 12/2006 | Mumper et al. |
| 7,226,581 | B2 | 6/2007 | Traynor et al. |
| 7,226,582 | B2 | 6/2007 | Traynor et al. |
| 7,258,874 | B2 * | 8/2007 | Barbe et al. ................... 424/501 |
| 7,563,451 | B2 | 7/2009 | Lin et al. |
| 2002/0187347 | A1 * | 12/2002 | Halas et al. ................... 428/403 |
| 2003/0157330 | A1 | 8/2003 | Ostafin et al. |
| 2004/0091411 | A1 | 5/2004 | Modrek-Najafabadi |
| 2006/0018966 | A1 | 1/2006 | Lin et al. |
| 2006/0167147 | A1 | 7/2006 | Asgari |
| 2006/0173709 | A1 | 8/2006 | Traynor et al. |
| 2006/0292345 | A1 | 12/2006 | Dave et al. |
| 2007/0036736 | A1 * | 2/2007 | Kalla et al. ...................... 424/63 |
| 2007/0292676 | A1 | 12/2007 | Naigertsik et al. |
| 2008/0112904 | A1 | 5/2008 | Traynor et al. |
| 2008/0233509 | A1 | 9/2008 | Keoshkerian et al. |
| 2008/0317795 | A1 * | 12/2008 | Traynor et al. ............... 424/401 |
| 2010/0016200 | A1 | 1/2010 | Nagare et al. |
| 2010/0143422 | A1 | 6/2010 | Popplewell et al. |
| 2010/0247660 | A1 | 9/2010 | Lei et al. |

* cited by examiner

*Primary Examiner* — James J Seidleck
*Assistant Examiner* — S. Camilla Pourbohloul
(74) *Attorney, Agent, or Firm* — One3 IP Management, P.C.; Dean G. Stathakis; Peter D. Weinstein

(57) ABSTRACT

This invention relates to a method for forming hollow silica-based particles suitable for containing one or more active ingredients or for containing other smaller particles which may include one or more active ingredients. In the method, an emulsion is prepared including a continuous phase that is polar or non-polar, and a dispersed phase comprising droplets including (i) a polar active ingredient when the continuous phase is non-polar or (ii) a non-polar active ingredient when the continuous phase is polar; and a prehydrolyzed silica precursor is added to the emulsion such that the silica precursor can be emulsion templated on the droplets to form hollow silica-based particles.

18 Claims, No Drawings

CERAMIC ENCAPSULATION WITH CONTROLLED LAYERING BY USE OF PREHYDROLYZED FUNCTIONALIZED SILANES

CROSS-REFERENCES TO RELATED APPLICATIONS

This application claims priority from U.S. Patent Application No. 61/358,737 filed Jun. 25, 2010.

STATEMENT REGARDING FEDERALLY SPONSORED RESEARCH

Not Applicable.

BACKGROUND OF THE INVENTION

1. Field of the Invention

This invention relates to a method for forming hollow silica-based particles suitable for containing one or more active ingredients or for containing other smaller particles which can include one or more active ingredients.

2. Description of the Related Art

One approach to providing an active ingredient to a surface, such as the skin, is to encapsulate the active ingredient in order to protect the active ingredient, control the release of the active ingredient, and/or modify the function of the active ingredient. Methods for encapsulation of an active ingredient, such as sol-gel encapsulation, are known in the art. See, for example U.S. Patent Application Publication No. 2008/0317795 to Traynor et al.

Even with the advances in the art described in U.S. 2008/0317795, there is still a need for further improved encapsulation techniques.

SUMMARY OF THE INVENTION

The present invention provides a method for forming silica-based particles that encapsulate one or more active ingredients or encapsulate other smaller particles which can include one or more active ingredients.

The method of the invention can use an oil in water emulsion that includes an aqueous continuous phase; a dispersed phase comprising droplets including a non-polar material and/or one or more oils; and a prehydrolyzed silica precursor. In one form, the prehydrolyzed silica precursor is a silane having at least one alkoxy group that has been converted to a hydroxyl group. In another form, the prehydrolyzed silica precursor is a silane having a functional group selected from substituted or unsubstituted alkyls, substituted or unsubstituted aryls, alcohols, amines, aldehydes, acids, esters, and groups including an unsaturated bond, and having at least one alkoxy group that has been converted to a hydroxyl group by hydrolysis. The oil in water emulsion can further include a second different silica precursor, wherein the prehydrolyzed silica precursor and the second silica precursor (typically not prehydrolyzed) can be emulsion templated on the droplets to form the silica-based particles. The present invention also provides an emulsion templated silica particle formed from the oil in water emulsion of the invention wherein the silica particle can be modified from a continuously formed shell to a partially formed hollow shell by adjusting a ratio of the prehydrolyzed silica precursor and the second silica precursor in the emulsion.

Alternatively, the method of the invention can use a water-in-oil emulsion that includes a non-polar, aqueous immiscible, "oil" continuous external phase; a dispersed internal phase comprising droplets including a polar active ingredient and optionally one or more other polar materials such as water; and a prehydrolyzed silica precursor. In one form, the prehydrolyzed silica precursor is a silane having at least one alkoxy group that has been converted to a hydroxyl group. In another form, the prehydrolyzed silica precursor is a silane having a functional group selected from substituted or unsubstituted alkyls, substituted or unsubstituted aryls, alcohols, amines, aldehydes, acids, esters, and groups including an unsaturated bond, and having at least one alkoxy group that has been converted to a hydroxyl group by hydrolysis. The water-in-oil emulsion can further include a second different silica precursor, wherein the prehydrolyzed silica precursor and the second silica precursor (typically not prehydrolyzed) can be emulsion templated on the droplets to form the silica-based particles. The present invention also provides an emulsion templated silica particle formed from the water-in-oil emulsion of the invention wherein the silica particle can be modified from a continuously formed shell to a partially formed hollow shell by adjusting a ratio of the prehydrolyzed silica precursor and the second silica precursor in the emulsion.

In either the oil-in-water emulsion or the water-in-oil emulsion, the silica precursor or silica precursors can be emulsion templated on the droplets to form the silica-based particles. The present invention also provides a templated silica particle formed from the oil-in-water emulsion or water-in-oil emulsion of the invention wherein the silica particle can be modified from a continuously formed shell to a partially formed hollow shell by adjusting a ratio of the prehydrolyzed silica precursor and the second silica precursor in the emulsion.

The present invention also provides an oil-in-water emulsion or water-in-oil emulsion for making silica coated particles. The oil-in-water emulsion or water-in-oil emulsion can include a surfactant component comprising a surfactant selected from anionic surfactants, nonionic surfactants, cationic surfactants, nonionic surfactants, and mixtures thereof, each surfactant in the surfactant component being above or below a critical micelle concentration of each surfactant; a continuous phase (i.e., water in the oil-in-water emulsion, or oil in the water-in-oil emulsion) that forms droplets of a dispersed phase (i.e., oil in the oil-in-water emulsion, or water in the water-in-oil emulsion); a first prehydrolyzed organically modified silica precursor having a carbon atom and having a first functional group that is capable of further reaction, and a second organically modified silica precursor having a carbon atom that is combined with the first organically modified silica precursor and having a second functional group, wherein the carbon atom of the second precursor and the second functional group are in a ratio from 1 to 99 to 99 to 1, and wherein the first prehydrolyzed organically modified silica precursor and the second organically modified silica precursor can be reacted to form precipitated silica shells around the droplets which act as templates. Without intending to be bound by theory, it is believed that above the critical micelle concentration of each surfactant, more surfactant will be at the surface of the droplets and monodisperse particles will be formed. Below the critical micelle concentration of each surfactant, less surfactant will be at the surface of the droplets, and a larger number of particles will be produced.

The hollow silica-based particles of the invention are suitable for encapsulating one or more active ingredients. Non-limiting example products in which the particles including an active ingredient can be used include: cosmetic products, such as skin cream and sunscreen formulations; detergent products such as laundry wash products, household cleaners, shampoos, hair conditioners and bleaches; and oral hygiene products such as toothpastes. Depending upon the product and its use, the particles may be employed to protect the active ingredient against loss by evaporation during storage or against chemical degradation by other ingredients in the formulation, to improve the targeting of materials in use (e.g., perfume deposition onto fabrics during washing), to assist controlled delivery through heat or dissolution, or to extend activity (e.g. of a fragrance or flavoring) through controlled delivery and evaporation.

In one version of the method, an emulsion is prepared including a continuous phase that is polar or non-polar, and a dispersed phase comprising droplets including (i) a polar active ingredient when the continuous phase is non-polar or (ii) a non-polar active ingredient when the continuous phase is polar; and a prehydrolyzed silica precursor is added to the emulsion such that the prehydrolyzed silica precursor can be emulsion templated on the droplets to form hollow silica-based particles. Before hydrolysis the silica precursor preferably has the general formula (I):

$$R^1_x\text{—Si—}(OR^2)_y \qquad (I)$$

wherein $R^1$ is selected from substituted and unsubstituted alkyl, substituted and unsubstituted aryl, alcohols, amines, amides, aldehydes, acids, esters, and functional groups having an unsaturated carbon-carbon bond, $R^2$ is an alkyl group, $x+y=4$, and $y=1$, 2 or 3. $R^1$ and/or $R^2$ can be substituted or unsubstituted, branched or unbranched, $C_1$ to $C_{1000}$ alkyl, or $C_1$ to $C_{100}$ alkyl, or $C_1$ to $C_{50}$ alkyl, or $C_1$ to $C_{25}$ alkyl, or $C_1$ to $C_{10}$ alkyl, or $C_1$ to $C_5$ alkyl.

A second silica precursor can be added to the emulsion such that the second silica precursor can be emulsion templated on the droplets or deposited on the hollow silica-based particles to form hollow silica-based particles. The second silica precursor has the general formula (II):

$$R^3_m\text{—Si—}(OR^4)_n \qquad (II)$$

wherein $R^3$ is selected from substituted and unsubstituted alkyl, substituted and unsubstituted aryl, alcohols, amines, amides, aldehydes, acids, esters, and functional groups having an unsaturated carbon-carbon bond, $R^4$ is an alkyl group, $m+n=4$, and $m=0$, 1, 2 or 3. The prehydrolyzed silica precursor and the second silica precursor can be added in a ratio from 1:99 to 99:1, or 1:50 to 50:1, or 1:25 to 25:1, or 1:10 to 10:1, or 1:5 to 5:1, or 1:2 to 2:1.

A third silica precursor can be added to the emulsion such that the third silica precursor can be emulsion templated on the droplets or deposited on the hollow silica-based particles to form hollow silica-based particles, wherein the third silica precursor has the general formula (III):

$$R^5_a\text{—Si—}(OR^6)_b \qquad (III)$$

wherein $R^5$ is selected from substituted and unsubstituted alkyl, substituted and unsubstituted aryl, alcohols, amines, amides, aldehydes, acids, esters, and functional groups having an unsaturated carbon-carbon bond, $R^6$ is an alkyl group, $a+b=4$, and $a=0$, 1, 2 or 3. The prehydrolyzed silica precursor and the third silica precursor can be added in a ratio from 1:99 to 99:1, or 1:50 to 50:1, or 1:25 to 25:1, or 1:10 to 10:1, or 1:5 to 5:1, or 1:2 to 2:1. The second silica precursor and the third silica precursor can be added in a ratio from 1:99 to 99:1, or 1:50 to 50:1, or 1:25 to 25:1, or 1:10 to 10:1, or 1:5 to 5:1, or 1:2 to 2:1.

It is an advantage of the invention to provide a method for encapsulation of an active ingredient in hollow silica-based particles in which unencapsulated particles formed in the method are minimized.

It is another advantage of the invention to provide a method for encapsulation of an active ingredient in hollow silica-based particles in which the particles do not need to be post-loaded with the active ingredient.

It is another advantage of the invention to provide a method for encapsulation of an active ingredient in hollow silica-based particles in which the reaction time is minimized in relation to other encapsulation methods.

It is another advantage of the invention to provide a method for encapsulation of an active ingredient in hollow silica-based particles in which Stoeber particles are minimized.

It is another advantage of the invention to provide a method for encapsulation of an active ingredient in hollow silica-based particles in which the resulting particles do not become brittle when dried.

It is another advantage of the invention to provide a method for encapsulation of an active ingredient in hollow silica-based particles in which the particles have a surface functionality or a chargeable surface for attachment of additional molecules.

These and other features, aspects, and advantages of the present invention will become better understood upon consideration of the following detailed description and appended claims.

DETAILED DESCRIPTION OF THE INVENTION

The invention provides a method of forming silica-based particles including an encapsulated non-polar or a polar active ingredient.

In one method of the invention, a non-polar active ingredient, a surfactant, and a polar phase (e.g., water) are combined and agitated to form an oil-in-water emulsion wherein the non-polar active ingredient and any optional non-polar diluent comprise a dispersed phase and the polar, aqueous material comprises a continuous phase. A prehydrolyzed silica precursor is added to the oil-in-water emulsion and mixed. Optionally, a second silica precursor is added to the oil-in-water emulsion and mixed. The silica precursor(s) hydrolyze and silica-based particles are formed which include the non-polar active ingredient. Thus, the oil-in-water emulsion provides for the encapsulation of one or more non-polar active ingredients. The methods of the invention can also be used in ternary, quaternary or higher emulsions. The emulsion templated silica particle can be modified from a continuously formed shell to a partially formed hollow shell by adjusting a ratio of the prehydrolyzed silica precursor and the second silica precursor in the emulsion. For example, the ratio of the prehydrolyzed silica precursor to the second silica precursor in the emulsion can be 0.1:1 to 100:1, more preferably 1:1 to 50:1, more preferably 5:1 to 40:1, and more preferably 10:1 to 30:1.

The prehydrolyzed silica precursor is typically formed in water at pH below 7, preferably a pH below 5, and most preferably a pH below 3. Various acids such as hydrochloric acid can be used as the pH adjuster. The alcohol byproduct can be removed before emulsion templating using the prehydrolyzed silica precursor. Excess alcohol can cause the formation of Stoeber particles. The emulsion templating reaction is preferably undertaken at a pH above 7, preferably a pH of 9-12 and most preferably a pH of 10-11. The prehydrolyzed silica precursor is deprotonated and therefore negative at basic pH. The negative charge can serve to keep the prehydrolyzed silica precursor out of polar active ingredients in dispersed polar droplets. The preferred version of the invention uses a non-polar active ingredient as the prehydrolyzed silica precursor is more negative at basic pH and seeks to stay away from the non-polar active ingredient in the droplets. Thus, the prehydrolyzed silica precursor can form a particle with no residual silane in the hollow core.

Various non-polar active ingredients can be used in the invention depending on the final use for the silica-based particles. Non-limiting examples for the active ingredient include sunscreens, steroidal anti-inflammatory actives, analgesic actives, antifungals, antibacterials, antiparasitics, antivirals, anti-allergenics, anti-cellulite additives, medicinal actives, skin rash, skin disease and dermatitis medications, insect repellant actives, antioxidants, hair growth promoter, hair growth inhibitor, hair bleaching agents, deodorant compounds, sunless tanning actives, skin lightening actives, anti-acne actives, anti-skin wrinkling actives, anti-skin aging actives, vitamins, nonsteroidal anti-inflammatory actives, anesthetic actives, anti-pruritic actives, anti-microbial actives, dental care agents, personal care agents, nutraceuticals, pharmaceuticals, fragrances, antifouling agents, pesticides, lubricants, etchants, and mixtures and combinations thereof. In one example embodiment, the non-polar active ingredient is a fragrance. In another example embodiment, the non-polar active ingredient is a sunscreen.

In another method of the invention, a polar active ingredient, a surfactant, and a non-polar aqueous immiscible oil are combined and agitated to form a water-in-oil emulsion wherein the polar active ingredient and any optional polar diluent comprise a dispersed phase and the non-polar, aqueous immiscible, "oil" comprise a continuous phase. A prehydrolyzed silica precursor is added to the water-in-oil emulsion and mixed. Optionally, a second silica precursor is added to the water-in-oil emulsion and mixed. The silica precursor(s) hydrolyze and silica-based particles are formed which include the polar active ingredient. Thus, the water-in-oil emulsion provides for the encapsulation of one or more polar active ingredients. The methods of the invention can also be used in ternary, quaternary or higher emulsions. In this method of the invention, a unique emulsion system is formed in the oily continuous phase that stabilizes the emulsion, preventing the coalescence of the polar droplets while the organic silica precursor is reacting.

A polar active ingredient is generally an ingredient that is soluble in water or in aqueous solution. The polar ingredient may be insoluble or sparingly soluble in an oil such as mineral oil, palm oil, or silicone oil. The polar diluent can be water and an alkanol such as ethanol. The polar active ingredient can comprise all or part of the core. By sparingly soluble, we mean very low solubilities such as 0.5 g per liter or lower.

Various polar active ingredients can be used in the invention depending on the final use for the silica-based particles. Non-limiting examples for the active ingredient include sunscreens, steroidal anti-inflammatory actives, analgesic actives, antifungals, antibacterials, antiparasitics, anti-virals, anti-allergenics, anti-cellulite additives, medicinal actives, skin rash, skin disease and dermatitis medications, insect repellant actives, antioxidants, hair growth promoter, hair growth inhibitor, hair bleaching agents, deodorant compounds, sunless tanning actives, skin lightening actives, anti-acne actives, anti-skin wrinkling actives, anti-skin aging actives, vitamins, nonsteroidal anti-inflammatory actives, anesthetic actives, anti-pruritic actives, anti-microbial actives, dental care agents, personal care agents, nutraceuticals, pharmaceuticals, fragrances, antifouling agents, pesticides, lubricants, etchants, and mixtures and combinations thereof. In one example embodiment, the polar active ingredient is a fragrance. In another example embodiment, the polar active ingredient is a sunscreen.

The invention also provides an emulsion for forming silica-based particles. The emulsion includes a continuous phase that is polar or non-polar; a dispersed phase comprising droplets including (i) a polar active ingredient when the continuous phase is non-polar or (ii) a non-polar active ingredient when the continuous phase is polar; a prehydrolyzed silica precursor; and a second silica precursor, wherein the prehydrolyzed silica precursor and the second silica precursor can be emulsion templated on the droplets to form the silica-based particles. The droplets initiate reaction of the prehydrolyzed silica precursor and the second silica precursor at interfaces between the droplets and the continuous phase.

The prehydrolyzed silica precursor can be a silane having a functional group selected from substituted or unsubstituted alkyls, substituted or unsubstituted aryls, alcohols, amines, aldehydes, acids, esters, and groups including an unsaturated bond. In one form, the prehydrolyzed silica precursor is cationic.

The dispersed phase can include a compound to control viscosity. The compound in the dispersed phase can be selected from water soluble polymers, salts, alcohols, glycols, alkylene ethoxylates, and mixtures thereof. The continuous phase can include a compound to control viscosity. The compound in the continuous phase can be selected from oil soluble polymers, waxes, fatty alcohols, triglycerides, fatty acids, fatty amines, esters, hydrocarbons, and mixtures thereof.

The emulsion can further comprise a surfactant selected from cationic, anionic, nonionic and amphoteric surfactants. The emulsion can have charge associated with the surfactant to help speed up the reaction at interfaces between the droplets and the continuous phase by targeting and directing precursor formation at interfaces between the droplets and the continuous phase in a quicker fashion. The surfactant can be introduced to the emulsion below a critical micelle concentration of the surfactant for precursor interface interaction. The surfactant can be introduced to the emulsion above a critical micelle concentration of the surfactant. A second surfactant can be introduced to the emulsion below a critical micelle concentration of the second surfactant for precursor interface interaction, wherein the second surfactant is selected from cationic, anionic, nonionic and amphoteric surfactants. The second surfactant can be introduced to the emulsion below a critical micelle concentration of the second surfactant for precursor interface interaction. The second surfactant can be introduced to the emulsion above a critical micelle concentration of the second surfactant for precursor interface interaction.

The surfactant can be added above a critical micelle concentration of the surfactant to stabilize the particles and then diluted to reduce the level of surfactant to maintain the level below the critical micelle concentration of the surfactant before the precursors are added for precursor interaction.

A charged polymer can be added to the emulsion. Preferably, the charged polymer is cationic. A ratio of the active ingredient to the charged polymer can be 1:1 to 30:1, 1:1 to 20:1, or 1:1 to 10:1, or 1:1 to 5:1. The charged polymer can be in the continuous phase or the dispersed phase comprising the droplets. When the charged polymer is in the continuous phase, it can provide a coating on the outside surface of the formed silica-based particles. When the charged polymer is in the droplets, it can provide a coating on the inside surface of the formed silica-based particles. The charged polymer can have 2 to 1000, or 5 to 500, or 10 to 100, or 25 to 50 repeat units. The charged polymer can have up to 1,000,000 repeat units. The charged polymer can alkoxylated, preferably ethoxylated, with 1-100 moles of alkoxy groups. A non-limiting example charged polymer is MERQUAT 550 (an aqueous solution of a highly charged cationic copolymer of 30 mole % diallyl dimethyl ammonium chloride and 70 mole % acrylamide).

At least one of the prehydrolyzed silica precursor and the second silica precursor can have multiple functionality. At least one of the prehydrolyzed silica precursor and the second silica precursor can have functional groups capable of preventing or limiting aggregation of the particles. At least one of the prehydrolyzed silica precursor and the second silica precursor can include a functional group that allows for attachment of a polymer or other molecular complex to a surface of the particles by covalent linking. The prehydrolyzed silica precursor can include a functional group having a net charge to attract towards an opposite charge of the surfactant at interfaces between the droplets and the continuous phase. The prehydrolyzed silica precursor can include a functional group having a charge ratio to limit polar and non-polar penetrations through interfaces between the droplets and the continuous phase to allow better stabilization of the emulsion as well as assist in reactions.

At least one of the prehydrolyzed silica precursor and the second silica precursor can include a combination of functional groups, at least two of the combination of functional groups being selected from functional groups that allow for attachment of a polymer or other molecular complex to a surface of the particles by covalent linking, functional groups having a net charge to attract towards an opposite charge of a surfactant at interfaces between the droplets and the continuous phase, and functional groups having a charge ratio to limit polar and non-polar penetrations through interfaces between the droplets and the continuous phase to allow better stabilization of the emulsion as well as assist in reactions.

The particles prepared by the method can be spherical, and/or monopore. The emulsion can include two or more oils which remain as a core of a silica particle shell after drying. At least one oil remains in a silica particle shell after being washed. In one method, the particle shell formation occurs for 10 minutes to 48 hours, and the particles are precipitated out. After precipitation, the particles can be washed with a 0.1% to 10% solution of a monovalent salt, such as NaCl or KCl. This shrinks the pore size and maintains shape of the oil. The silica particles can be modified from a continuously formed shell to a partially formed hollow shell by adjusting a ratio of the prehydrolyzed silica precursor and the second silica precursor in the emulsion. The silica particle can lose its internal core due to partial formation from a limited molar ratio of the prehydrolyzed silica precursor and the second silica precursor. The silica particle can include a partially formed shell from aid of precursor hindrance from the functional groups on the precursor. The silica particle can allow for one or more particles of smaller size either with a pore or continuous shell to be present in the partially formed shell.

The particle can have functional groups capable of attaching a coating by covalent bonding, non-covalent bonding, ionic bonding, electrostatic attraction, or any other attachment mechanism which allows for coating proximity within sub-nanometer ranges to 500 microns. The coating can comprise a polymeric material.

In another version of the method, the particles have multiple layering effects while trapping an active material inside these layers. The particle can have 1 to 100 layers of silica deposited when the first silica precursor and the second silica precursor are templated on a droplet. The particle can burst upon friction and release a payload contained within the particle. The particle can remain intact within environments of pH ranges from 0.01-14. The particle can be chemically altered and open for diffusion of a payload contained within the particle.

The prehydrolyzed silica precursor can leaves a first shell thickness of 1 nanometer to 500 nanometers for the particle when the prehydrolyzed silica precursor and the second silica precursor are templated on a droplet. The second silica precursor bonds to the first shell to create an outer layer such that the first shell and the outer layer together have a thickness in the range of 1 nanometer to 1 micron. The particle can form from the prehydrolyzed silica precursor and the second silica precursor making a shell with a thickness of 1 nanometer to 5 microns. The particle can have an overall size of 10 nanometers to 250 microns. The particle can include a polar or non-polar active ingredient droplet having a size of 1 nanometer to 200 microns.

The particle can maintain a template volume of greater than 0.01%. The particle can maintain a template volume up to 100% loading. The particle can maintain greater than 0.01% of a loaded material if the loaded material dissipates or leaches from the particle. The particle allows for complete release of a payload material from the particle when the particle is intact or ruptured. The particle can release one layer of a loaded material at a time. The particle releases multiple layers of a loaded material at a time. The particle can release a loaded material due to coating dissociation. The particle can remain completely or partially intact due to a coating on the particle.

A templated silica particle formed from the method of the invention can be dispersed in a carrier of polarity opposite to the active ingredient, and the particle can release the active ingredient due to bulk phase evaporation of the carrier. The particle can remain completely or partially intact due to a coating on the particle. The particle can include an oil with a mixture of solids, semi solids, or other liquids or gases. The particle can have water soluble constituents mixed in an oil forming the emulsion for the templating.

In one form, the templated silica particle has a zeta potential ranging from −80 mV to 150 mV. The zeta potential can be measured on a Zetasizer instrument from Malvern Instruments, Malvern, UK, or on a ZetaPlus or ZetaPALS instrument from Brookhaven Instruments, Holtsville, N.Y. In some embodiments, the templated silica particles have a zeta potential of at least about 5, 10, 12, 14, 16, 18, 20, 25, 30, 35, 40, 45, 50, 55, 60, 65, 70, 80, 90 or 100 mV. In some embodiments, the templated silica particles have a zeta potential of no more than about 15, 20, 25, 30, 35, 40, 45, 50, 55, 60, 65, 70, 80, 90, 100, or 150 mV. In some embodiments the zeta potential is between 10 and 70 mV, between 20 and 65 mV, between 25 and 65 mV, between 30 and 60 mV, between 30 and 100 mV, between 40 and 80 mV, between 70 and 100 mV or between 40 and 55 mV.

The invention also provides an emulsion for making silica-based particles. The emulsion includes a continuous phase that is polar or non-polar; a dispersed phase comprising droplets including (i) a polar active ingredient when the continuous phase is non-polar or (ii) a non-polar active ingredient when the continuous phase is polar; a prehydrolyzed silica precursor, wherein the prehydrolyzed silica precursor is an organically modified silica precursor with at least one carbon, wherein the prehydrolyzed silica precursor can be templated on the droplets to make the silica-based particles. The organically modified silica precursor can include at least one carbon on two, three or all four bonding sites of silicon in the organically modified silica precursor. The organically modified silica precursor can include two or more of the same organically modified groups on bonding sites of the silicon in the organically modified silica precursor.

The invention also provides another emulsion for making silica-based particles. The emulsion includes a continuous phase that is polar or non-polar; a dispersed phase comprising droplets including (i) a polar active ingredient when the continuous phase is non-polar or (ii) a non-polar active ingredient when the continuous phase is polar; a surfactant component comprising a surfactant selected from anionic surfactants, nonionic surfactants, cationic surfactants, nonionic surfactants, and mixtures thereof wherein each surfactant in the surfactant component is at or below a critical micelle concentration of each surfactant; a first prehydrolyzed organically modified silica precursor having at least one carbon atom and having a first functional group that is capable of further reaction, and a second organically modified silica precursor having at least one carbon atom that is combined with the first prehydrolyzed organically modified silica precursor and having a second functional group, wherein the at least one carbon atom and the second functional group are in a ratio from 1 to 99 to 99 to 1, wherein the first prehydrolyzed organically modified silica precursor and the second organically modified silica precursor can be reacted to form precipitated silica shells around the droplets which act as templates. The first functional group can be selected from alcohols, amines, aldehydes, acids, esters, and groups including an unsaturated bond. The second functional group can be selected from alcohols, amines, aldehydes, acids, esters, and groups including an unsaturated bond.

The silica shell can include an alcohol functional group on a surface of the silica shell that can be further reacted with: (i) an acid, an acid anhydride or an acid chloride to form an ester, or (ii) a hydrosilane that reacts to form a siloxy group that will link alkyl siloxane compounds to the shell surface, or (iii) a chlorosilane that reacts to form a siloxy group that will link alkyl siloxane compounds to the shell surface, or (iv) an epoxide that will react to form an ether group that will link alkyl groups (with or without additional functional groups) to the silica shell surface.

The silica shell can include an amine functional group on a surface of the silica shell that can be further reacted with: (i) an acid, an acid anhydride or an acid chloride to form an amide, or (ii) an alkylhalide (or dimethyl sulfate or diethyl sulfate) to form a 2°,3° amine or a quaternary ammonium salt that will link an alkyl group(s) (with or without additional functional groups) to the silica sphere surface, or (iii) an amine salt with an epoxide that will react to form a 2°,3° ammonium salt or a quaternary ammonium salt group that will link alkyl group(s) (with or without additional functional groups) to the silica shell surface, or (iv) an aldehyde or a ketone that will react to form an imine or Schiff base compounds that will link alkyl groups (with or without additional functional groups) to the silica shell surface, or (v) an acid to form an ammonium salt on the silica sphere surface to impart a positive (cationic) charge to the silica sphere surface.

The silica shell can include an aldehyde functional group on a surface of the silica shell that can be further reacted with: (i) an aldehyde, ketone or ester to form an aldol condensation product that will link alkyl groups (with or without additional functional groups) to the silica shell surface, or (ii) an amine to form an imine or Schiff base compounds that will link alkyl groups (with or without additional functional groups) to the silica shell surface.

The silica shell can include an acid functional group on a surface of the silica shell that can be further reacted with: (i) an alcohol to form an ester that will link alkyl groups (with or without additional functional groups) to the silica shell surface, or (ii) an amine to form an amide that will link alkyl groups (with or without additional functional groups) to the silica shell surface, or (iii) an amine to form an ionic ammonium salt that will link alkyl groups (with or without additional functional groups) to the silica shell surface, or (iv) a base to form an ionized acid group that will impart a negative (anionic) charge to the silica sphere surface.

The silica shell can include an ester functional group on a surface of the silica shell that can be further reacted with: (i) an alcohol (or acid) group as required to transesterify to form a new ester linkage that will join alkyl groups (with or without additional functional groups) to the silica shell surface, or (ii) an amine to form an amide that will link alkyl groups (with or without additional functional groups) to the silica shell surface.

The silica shell can include an unsaturated functional group on a surface of the silica shell that can be further reacted with: (i) a hydrosilane that reacts to form an alkylsilane linkage that will join alkyl siloxane compounds to the shell surface, or (ii) an additional unsaturated compound (along with appropriate catalysts or reaction conditions) to polymerize thereby attaching a polymer (that may have additional functional groups) to the silica shell surface.

The silica shell can include a polymer attached to the first functional group and/or the second functional group on a surface of the silica.

Active ingredients can be encapsulated within the hollow silica-based particles of the invention. The particles can be viewed as having two parts, the core and the shell. The core contains the active ingredient, while the shell surrounds and protects the core. The core materials used in the invention can be solid or liquid, and if liquid, can be, for example, in the form of a pure compound, solution, dispersion or emulsion. The shell material can be a silica-based shell. The shell can be made permeable, semi-permeable or impermeable. Permeable and semi-permeable shells can be used for release applications. A permeable shell can be a shell including one or more passageways that extend from an inner surface of the shell (which is around the core) and the outer surface of the shell. Semi-permeable shells can be made to be impermeable to the core material but permeable to low molecular-weight liquids and can be used to absorb substances from the environment and to release them again when brought into another medium. The impermeable shell encloses the core material. To release the content of the core material, the shell must be ruptured.

The ceramic shells are prepared by a sol-gel based process in which a silica precursor is used. There are many silica precursors which can used in the present invention. For example, the silica precursor can be a silicate (silicon acetate, silicic acid or salts thereof), a silsequioxanes or poly-silsequioxanes, silicon alkoxides (e.g., from silicon methoxide to silicon octadecyloxide), and functionalized alkoxides (such as ethyltrimethoxysilane, aminopropyltriethoxysilane, vinyltrimethoxysilane, diethyldiethoxysilane, diphenyldiethoxysilane, etc). Further specific examples of silica precursors include tetramethoxysilane (TMOS), tetraethoxysilane (TEOS), tetrabutoxysilane (TBOS), tetrapropoxysilane (TPOS), polydiethoxysilane, methyltrimethoxysilane, methyltriethoxysilane, ethyltriethoxysilane, phenyltriethoxysilane, octylpolysilsesquioxane and hexylpolysilsesquioxane. The silica precursor may include, for example, from one to four alkoxide groups each having from 1 or more oxygen atoms, and from 1 to 18 carbon atoms, more typically from 1 to 5 carbon atoms. The alkoxide groups may be replaced by one or more suitable functional groups. Examples of functional groups attached to silica precursors include substituted or unsubstituted alkyls, substituted or unsubstituted aryls, alcohols, amines, amides, aldehydes, acids, esters, and groups including an unsaturated bond. Thus, an organically modified silica precursor can be used. An organically modified silica precursor can be a silica precursor wherein one or two (out of four) of the alkoxysilane groups has been replaced by organic groups like substituted or unsubstituted alkyls, substituted or unsubstituted aryls, alcohols, amines, amides, aldehydes, acids, esters, and groups including an unsaturated bond. The organic groups can be polar or non-polar. The polar or non-polar group serves to drive the polar or non-polar group of the silica precursor to the interface between the dispersed phase and the continuous phase. The processing is based on the hydrolysis and condensation of the silica precursors. Water is thus typically used as the condensing agent.

Various surfactants can be used in the method of the invention. In order to form an oil-in-water emulsion of the invention, surfactants with an HLB value above about 8 are generally used. In some cases, multiple surfactants are used as a blend. Where there are multiple surfactants, the combined HLB of the surfactants is generally used. The HLB of the surfactant or surfactants is between, for example, 7 and 13, 8 and 12, 9 and 11, 9.5 and 10.5. In some embodiments, the HLB of the surfactants is 8, 8.5, 9, 9.5, 10, 10.5, 11, 11.5, or 12. Surfactants suitable for forming the oil-in-water emulsion include anionic, non-ionic, cationic, and zwitterionic surfactants. Non-limiting example surfactants include: anionic—sodium oleate, sodium dodecyl sulfate, sodium diethylhexyl sulfosuccinate, sodium dimethylhexyl sulfosuccinate, sodium di-2-ethylacetate, sodium 2-ethylhexyl sulfate, sodium undecane-3-sulfate, sodium ethylphenylundecanoate, carboxylate soaps; cationic—dimethylammonium and trimethylammonium surfactants of chain length from 8 to 20 and with chloride, bromide or sulfate counterion, myristyl-gammapicolinium chloride and relatives with alkyl chain lengths from 8 to 18, benzalkonium benzoate, double-tailed quaternary ammonium surfactants with chain lengths between 8 and 18 carbons and bromide, chloride or sulfate counterions, stearyl dimethyl benzyl ammonium chloride; nonionic: surfactants of the form $C_n(EO)_m$ where the alkane chain (C) length n is from 6 to 20 carbons and the average number of ethylene oxide (EO) groups m is from 2 to 80, ethoxylated cholesterol; zwitterionics and semipolars—N,N,N-trimethylaminodecanoimide, amine oxide surfactants with alkyl chain length from 8 to 18 carbons, dodecyldimethylammoniopropane-1-sulfate, dodecyldimethylammoniobutyrate, dodecyltrimethylene di(ammonium chloride), decylmethylsulfonediimine, dimethyleicosylammoniohexanoate and relatives of these zwitterionics and semipolars with alkyl chain lengths from 8 to 20.

In order to form the water-in-oil emulsion of the invention, surfactants with an HLB value below about 8 are generally used. In some cases, multiple surfactants are used as a blend. Where there are multiple surfactants, the combined HLB of the surfactants is generally used. The HLB of the surfactant or surfactants is between, for example, 2 and 7, 3 and 6, 4 and 5, or 3.5 and 4.5. In some embodiments, the HLB of the surfactants is 2, 2.5, 3, 3.5, 4, 4.5, 5, 5.5 or 6. Surfactants suitable for forming the water-in-oil emulsion include anionic, non-ionic, cationic, and zwitterionic surfactants. Non-limiting example surfactants include: anionic—sodium oleate, sodium dodecyl sulfate, sodium diethylhexyl sulfosuccinate, sodium dimethylhexyl sulfosuccinate, sodium di-2-ethylacetate, sodium 2-ethylhexyl sulfate, sodium undecane-3-sulfate, sodium ethylphenylundecanoate, carboxylate soaps; cationic—dimethylammonium and trimethylammonium surfactants of chain length from 8 to 20 and with chloride, bromide or sulfate counterion, myristyl-gammapicolinium chloride and relatives with alkyl chain lengths from 8 to 18, benzalkonium benzoate, double-tailed quaternary ammonium surfactants with chain lengths between 8 and 18 carbons and bromide, chloride or sulfate counterions; nonionic: surfactants of the form $C_n(EO)_m$ where the alkane chain (C) length n is from 6 to 20 carbons and the average number of ethylene oxide (EO) groups m is from 2 to 80, ethoxylated cholesterol; zwitterionics and semipolars—N,N,N-trimethylaminodecanoimide, amine oxide surfactants with alkyl chain length from 8 to 18 carbons, dodecyldimethylammoniopropane-1-sulfate, dodecyldimethylammoniobutyrate, dodecyltrimethylene di(ammonium chloride), decylmethylsulfonediimine, dimethyleicosylammoniohexanoate and relatives of these zwitterionics and semipolars with alkyl chain lengths from 8 to 20.

Cationic surfactants may be especially beneficial when used in the method of the invention. The prehydrolyzed silica precursor is deprotonated and therefore negative at basic pH. When a cationic surfactant is present at the dispersed phase-continuous phase interface, this drives the deprotonated prehydrolyzed silica precursor to the interface thereby speeding up the reaction time. In addition, any positive charges on functional groups of the prehydrolyzed silica precursor can drive further deprotonated prehydrolyzed silica precursor to the interface thereby speeding up the reaction time.

The silica-based particles can include the active ingredient within the core of the particle. In some cases, the active ingredient can perform its function while contained within the core of the particle. In some cases, the active ingredient must leave the core of the particle in order to perform its action. In some embodiments, the particles are produced such that the shell of the particle ruptures in order to release the active ingredient. In some cases, the surface onto which the particles are applied is pre-coated with an ingredient that reacts with the sol-gel particle in order to cause controlled breakage of the particles and release of the active ingredient. In some cases the surface can be post treated with a substance that either enhances or retards particle breakage.

The silica-based particles can be used in a wash-on formulation. As used herein, a "wash-on" formulation encompasses all cleansing vehicles applied to a surface. A wash-on formulation is generally applied to a surface in order to perform a cleaning function, and in addition to the cleaning aspect of the wash-on, a portion of the wash-on formulation remains on the surface to provide a function beyond cleaning. Exemplary forms of cleansing vehicles include, but are not limited to, liquid, bar, gel, foam, aerosol or pump spray, cream, lotion, stick, powder, or incorporated into a patch or a towelette. In addition, soapless cleansers may be used as well. The wash-on can be made into any suitable product form.

The silica-based particles can be used in a leave-on formulation. As used herein, a "leave-on" formulation is applied directly to a surface. A leave-on formulation may not perform a cleansing function. The leave-on can be, for example, a cream, lotion, gel, coating, paint, varnish, oil, spray, or powder. The leave-on formulations of the invention generally have a function that is performed or enhanced by the active that is delivered to the surface within the sol-gel particles.

The silica-based particles can be used in a bodywash formulation. As used herein, "bodywash" is a type of wash-on formulation that encompasses all cleansing vehicles applied to the body. Exemplary forms of cleansing vehicles include, but are not limited to, liquid, bar, gel, foam, aerosol or pump spray, cream, lotion, stick, powder, or incorporated into a patch or a towelette. In addition, soapless cleansers may be used as well. The bodywash can be made into any suitable product form. Thus, as used herein, "bodywash" includes, but is not limited to, a soap including liquid and bar soap; a shampoo; a hair conditioner; a shower gel; including an exfoliating shower gel; a foaming bath product (e.g. gel, soap or lotion); a milk bath; a soapless cleanser, including a gel cleanser, a liquid cleanser and a cleansing bar; moist towelletes; a body lotion; a body spray, mist or gel; bath effervescent tablets (e.g., bubble bath); a hand and nail cream; a bath/shower gel; a shower cream; a depilatory cream; a shaving product (e.g., a shaving cream, gel, foam or soap, an after-shave, after-shave moisturizer; and combinations thereof), and any other composition used for cleansing or post-cleansing application to the body, including the skin and hair. Especially useful as bodywashes in the invention are soaps, e.g., liquid soaps and bar soaps, and shampoos.

The particles of the invention can be used to produce compositions for agricultural, textile, industrial, transportation, marine, pharmaceutical, or personal care applications. The compositions can be applied to a broad range of surfaces. The particles contain active ingredients that perform a function when applied as part of the compositions of the present invention.

The sol-gel particles of the invention can be formulated to control whether or not there is penetration into the skin or other surface and if there is penetration, to what depth. In some cases the control of penetration can be influenced by the conditions of the skin such as pH, presence of film formers, and roughness. Where sunscreens are used, penetration into the skin is not generally desirable and the particles can be formulated to minimize or eliminate skin penetration. In some embodiments, such as where the active ingredient is a pigment or pharmaceutical on the skin, some amount of skin penetration is desired. In some embodiments, after application of the bodywash containing the active to the skin followed by rinsing, the active penetrates to an average of at least about 5 microns beneath the skin surface. The particles can be formulated such that the active will penetrate only to a given layer of the skin.

The skin can be seen to have three primary layers, the epidermis, which provides waterproofing and serves as a barrier to infection; the dermis, which serves as a location for the appendages of skin; and the hypodermis (subcutaneous adipose layer). In some embodiments, the active ingredient penetrates the epidermis. In some embodiments the active ingredient penetrates the dermis. In some embodiments, the active ingredient penetrates the hypodermis. The particles can thus be produced such that the contents of the particles, the active ingredients, are introduced into the blood stream. In some embodiments, the active penetrates to an average of at least about 10, 15, 20, 25, 30, 40, 50, 60, 70, 80, 90, 100, 120, or 150 microns beneath the skin surface. In some embodiments, after application of the leave-on or bodywash containing the active to the skin followed by rinsing, the active penetrates to an average of no more than about 30 microns beneath the skin surface. In some embodiments, the active penetrates to an average of no more than about 50, 40, 30, 25, 20, 15, 10, or 5 microns beneath the skin surface. In some embodiments, after application of the bodywash containing the active to the skin followed by rinsing, the active penetrates to an average of about 5 to about 50, or about 5 to about 40, or about 5 to about 30, or about 10 to about 40, or about 15 to about 40, or about 20 to about 40, or about 5, 10, 15, 20, 25, 30, 25, 40, 45, or 50 microns beneath the skin surface. Depth of penetration may be tested by tape stripping methods, as are well-known in the art. In some embodiments, the particles can assist in disrupting cell membranes in order to actively deliver active ingredients into the tissue or the blood. In some embodiments, the particles will be inert to the skin and will not cause disruption and penetration.

When the silica-based particles are used to encapsulate a perfume or fragrance as the active ingredient, various perfumes or fragrances can be used. For example, non-limiting examples of perfumes include: phenyl ethyl alcohol, linalool, geraniol, citronellol, cinnamic alcohol, benzyl acetate, linalyl acetate, amyl salicylate, benzyl salicylate, cinnamic aldehyde, anisaldehyde, citral, limonene, coumarin, eugenol, methyl eugenol, methyl cedrenyl ketone, patchouli, lavandin, ionone, amyl cinnamic aldehyde, orange oil, citronella, citronellal, citrathal, ethylene brassylate, phenyl ethyl acetate, oakmoss, hexyl salicylate, eucalyptol, and mixtures thereof.

The size of the silica-based particles formed is determined, at least in part, by the conditions of the reaction including the size of the original emulsion, and the conditions used for formation of the silica-based particles. A distribution of particle sizes can be obtained, or particles of a uniform size can be formed. The silica-based particles can also be fractionated into a desired size range after formation. Fractionation can be carried out by methods known in the art such as selective precipitation, or by using filters or sieves in order to pass a selected size range and retain the rest. The size of the silica-based particles can be modified in order to suit a particular application.

In some embodiments, the mean size of the silica-based particles is between 10 nanometers and 1 millimeter, between 10 nanometers and 1 µm, between 1 µm and 100 µm, between 10 µm and 50 µm, between 50 µm and 200 µm, or between 200 µm and 500 µm. In some embodiments, the mean size of the silica-based particles is between 1 nanometer and 10 nanometers, between 10 nanometers and 100 nanometers, between 100 nanometers and 1 µm, between 150 nanometers and 800 nanometers, between 1 µm and 5 µm, between 1 µm and 10 µm, between 5 µm and 10 µm, between 1 µm and 20 µm, between 10 µm and 20 µm, between 10 µm and 100 µm, between 100 µm and 1 millimeter, between 1 millimeter to 10 millimeters, or larger.

In some embodiments, the mean size of the silica-based particles is within plus or minus 10% of 1 nanometer, 10 nanometers, 25 nanometers, 50 nanometers, 75 nanometers, 90 nanometers, 100 nanometers, 250 nanometers, 500 nanometers, 750 nanometers, 900 nanometers, 1 µm, 5 µm, 10 µm, 25 µm, 50 µm, 75 µm, 90 µm, 100 µm, 250 µm, 500 µm, 750 µm, 900 µm, 1 millimeter, or larger. In some embodiments, the mean size of the silica-based particles is within plus or minus 50% of 1 nanometer, 10 nanometers, 25 nanometers, 50 nanometers, 75 nanometers, 90 nanometers, 100 nanometers, 250 nanometers, 500 nanometers, 750 nanometers, 900 nanometers, 1 µm, 5 µm, 10 µm, 25 µm, 50 µm, 75 µm, 90 µm, 100 µm, 250 µm, 500 µm, 750 µm, 900 µm, 1 millimeter, or larger.

In some embodiments, the mean size of the shell thickness of the silica-based particles is between 1 nanometer and 100 nanometers, between 2 nanometers and 60 nanometers. In some embodiments, the silica-based particles are monodisperse. When smaller particles are included in the core of the silica-based particle, the mean size of the smaller particles is preferably no more than about 50%, preferably less than about 25%, and more preferably less than about 10% of the diameter of the central core portion of the silica-based particle.

In fragrance applications, particles having a mean size of 800 nanometers to 80 microns and wall sizes of 20-100 nanometers are preferred.

The invention is further illustrated in the following Examples which are presented for purposes of illustration and not of limitation.

Example 1

Aminopropyltriethoxysilane was prehydrolyzed at a pH of 2 using hydrochloric acid to create aminopropyltrihydroxysilane. An emulsion was formed by homogenizing a mixture of 2.5 grams (1.5%) sodium dodecyl sulfate, 0.75 grams of oil fragrance, and 21.75 milliliters of water. This process ran for 30 minutes. An oil in water emulsion was formed with the desired oil droplet sizes. Ammonia was added at 1 milliliter to the emulsion solution as catalyst for the sol-gel reaction with stirring. Then 2.5 milliliters of aminopropyltrihydroxysilane was introduced for the silica shell formation around the surfactant stabilized oil droplets and the reaction solution was stirred for a time period of 2 hours. After the reaction was complete, a small volume of the reaction solution was transferred into a vial for washing with water using a centrifuge for three times. At the end of washing, this solution was used to prepare scanning electron microscope samples for investigation of the shell formation and size distribution. Complete hollow shells were identified.

Example 2

Aminopropyltriethoxysilane was prehydrolyzed at a pH of 2 using hydrochloric acid to create aminopropyltrihydroxysilane. An emulsion was formed by homogenizing a mixture of 0.0375 grams (10%) Incroquat™ stearyl dimethyl benzyl ammonium chloride, 0.75 grams of oil fragrance, and 21.2125 milliliters of water. This process ran for 30 minutes. An oil in water emulsion was formed with the desired oil droplet sizes. Ammonia was added at 1 milliliter to the emulsion solution as catalyst for the sol-gel reaction with stirring. Then 2.5 milliliters of aminopropyltrihydroxysilane was introduced for the silica shell formation around the surfactant stabilized oil droplets and the reaction solution was stirred for a time period of 2 hours. After the reaction was complete, a small volume of the reaction solution was transferred into a vial for washing with water using a centrifuge for three times. At the end of washing, this solution was used to prepare scanning electron microscope samples for investigation of the shell formation and size distribution. Complete hollow shells were identified.

Example 3

Phenyltriethoxysilane was prehydrolyzed at a pH of 2 using hydrochloric acid to create phenyltrihydroxysilane. An emulsion was formed by homogenizing a mixture of 0.075 grams (10%) Incroquat™ stearyl dimethyl benzyl ammonium chloride, 1.5 grams of oil fragrance, and 48.425 milliliters of water. This process ran for 30 minutes. An oil in water emulsion was formed with the desired oil droplet sizes. Ammonia was added at 2.5 milliliters to the emulsion solution as catalyst for the sol-gel reaction with stirring. Then 5 milliliters phenyltrihydroxysilane was introduced for the silica shell formation around the surfactant stabilized oil droplets and the reaction solution was stirred for a time period of 2 hours. After the reaction was complete, a small volume of the reaction solution was transferred into a vial for washing with water using a centrifuge for three times. At the end of washing, this solution was used to prepare scanning electron microscope samples for investigation of the shell formation and size distribution. Submicron hollow particles and many above 1 micron were identified.

Example 4

Phenyltriethoxysilane was prehydrolyzed at a pH of 2 using hydrochloric acid to create phenyltrihydroxysilane. An emulsion was formed by homogenizing a mixture of 0.075 grams (10%) Incroquat™ stearyl dimethyl benzyl ammonium chloride, 0.0375 grams (10%) of oil fragrance, and 24.2125 milliliters of water. This process ran for 30 minutes. An oil in water emulsion was formed with the desired oil droplet sizes. Ammonia was added at 1.25 milliliters to the emulsion solution as catalyst for the sol-gel reaction with stirring. Then 2 milliliter of a first silica precursor, phenyltrihydroxysilane, was introduced for the preliminary silica shell formation around the surfactant stabilized oil droplets and the reaction solution was stirred for a time period of 2 hours. After this step, 0.125 milliliters of a second silica precursor, tetraethoxysilane (TEOS), was introduced over 30 minutes under stirring for the thickening of the shell and then after some time the stirring was stopped and the reaction solution was allowed to sit for 1-2 days for the hollow silica-based particles. After the reaction was complete, a small volume of the reaction solution was transferred into a vial for washing with water using a centrifuge for three times. At the end of washing, this solution was used to prepare scanning electron microscope samples for investigation of the shell formation and size distribution. Thirty minutes after phenyltrihydroxysilane was added, most hollow particles were above 1 micron, although very polydispersed and some submicron particles were visible. After TEOS addition, particles maintained their size.

Example 5

Phenyltriethoxysilane was prehydrolyzed at a pH of 2 using hydrochloric acid to create phenyltrihydroxysilane. An emulsion was formed by homogenizing a mixture of 0.8 grams (10%) Triton™ X-100 non-ionic surfactant (Octylphenol Ethoxylate, R—$C_6H_4$—O—$(CH_2CH_2O)_x$—H where R=octyl (C8) and x=9.5 avg.), 1.5 grams of oil fragrance, and 47.7 milliliters of water. This process ran for 30 minutes. An oil in water emulsion was formed with the desired oil droplet sizes. Ammonia was added at 2.5 milliliters to the emulsion solution as catalyst for the sol-gel reaction with stirring. Then 4 milliliters phenyltrihydroxysilane was introduced for the silica shell formation around the surfactant stabilized oil droplets and the reaction solution was stirred for a time period of 2 hours. After the reaction was complete, a small volume of the reaction solution was transferred into a vial for washing with water using a centrifuge for three times. At the end of washing, this solution was used to prepare scanning electron microscope samples for investigation of the shell formation and size distribution. Complete hollow shells with many above 1 micron were identified.

Example 6

Phenyltriethoxysilane was prehydrolyzed at a pH of 2 using hydrochloric acid to create phenyltrihydroxysilane. An emulsion was formed by homogenizing a mixture of 0.075 grams (10%) Incroquat™ stearyl dimethyl benzyl ammonium chloride, 1.5 grams of oil fragrance, and 48.425 milliliters of water. This process ran for 30 minutes. An oil in water emulsion was formed with the desired oil droplet sizes. Ammonia was added at 2.5 milliliters to the emulsion solution as catalyst for the sol-gel reaction with stirring. Then 5 milliliters phenyltrihydroxysilane was introduced for the silica shell formation around the surfactant stabilized oil droplets and the reaction solution was stirred for a time period of 2 hours. After the reaction was complete, a small volume of the reaction solution was transferred into a vial for washing with water using a centrifuge for three times. At the end of washing, this solution was used to prepare scanning electron microscope samples for investigation of the shell formation and size distribution. Complete hollow shells with many above 1 micron and many above 10 microns were identified; however, the large shells are coated with thousands of smaller, submicron shells.

Example 7

Phenyltriethoxysilane was prehydrolyzed at a pH of 2 using hydrochloric acid to create phenyltrihydroxysilane. An emulsion was formed by homogenizing a mixture of 0.075 grams (10%) Incroquat™ stearyl dimethyl benzyl ammonium chloride, 1.5 grams (10%) of oil fragrance, and 48.425 milliliters of water. This process ran for 30 minutes. An oil in water emulsion was formed with the desired oil droplet sizes. Ammonia was added at 0.2 milliliters to the emulsion solution as catalyst for the sol-gel reaction with stirring. Then 5 milliliter of a first silica precursor, phenyltrihydroxysilane, was introduced for the preliminary silica shell formation around the surfactant stabilized oil droplets and the reaction solution was stirred for a time period of 2 hours. After this step, 0.25 milliliters of a second silica precursor, tetraethoxysilane (TEOS), was introduced over 30 minutes under stirring for the thickening of the shell and then after some time the stirring was stopped and the reaction solution was allowed to sit for 1-2 days for the hollow silica-based particles. After the reaction was complete, a small volume of the reaction solution was transferred into a vial for washing with water using a centrifuge for three times. At the end of washing, this solution was used to prepare scanning electron microscope samples for investigation of the shell formation and size distribution. Thirty minutes after phenyltrihydroxysilane was added, all hollow shells are above 1 micron, many 5-10 microns with no denting. Thirty minutes after TEOS, no major denting, however overall, particles are smaller than the phenyltrihydroxysilane step; most are around 1 micron with many submicron.

Thus, the invention provides a method for forming hollow silica-based particles suitable for containing one or more active ingredients or for containing other smaller particles which may include one or more active ingredients. The use of a prehydrolyzed functionalized silane can speed up reaction times while layering can be controlled by phenyl and other groups such as amine that can block the formation of silica layers, i.e., the thickness can be varied by blocking groups that stop reaction. The prehydrolyzed functionalized silanes can speed up reaction times while functional groups such as phenyls can align at interface and form pores, i.e., porosity is controlled by modified silanes. Also, the prehydrolyzed functionalized silanes can be added in a controlled molar ratio to the encapsulated active to form hollow core, monopore particles.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for forming hollow silica-based particles, the method comprising:
(a) preparing an emulsion including a continuous phase that is polar or non-polar, and a dispersed phase comprising droplets including (i) a polar active ingredient when the continuous phase is non-polar or (ii) a non-polar active ingredient when the continuous phase is polar; and
(b) adding a prehydrolyzed silica precursor to the emulsion such that the silica precursor can be emulsion templated on the droplets to form hollow silica-based particles, wherein the prehydrolyzed silica precursor is formed in water at pH below 7 and before hydrolysis the silica precursor has the general formula (I):

$$R^1_x\text{—Si—}(OR^2)_y \qquad (I)$$

wherein $R^1$ is selected from substituted and unsubstituted alkyl, substituted and unsubstituted aryl, alcohols, amines, amides, aldehydes, acids, esters, and functional groups having an unsaturated carbon-carbon bond, $R^2$ is an alkyl group, x+y=4, and y=1, 2 or 3, and after formation of the prehydrolyzed silica precursor, alcohol is removed before adding the prehydrolyzed silica precursor to the emulsion.

2. The method of claim 1 further comprising:
(c) adding a second silica precursor to the emulsion such that the second silica precursor can be emulsion templated on the droplets or deposited on the hollow silica-based particles to form hollow silica-based particles.

3. The method of claim 2 wherein:
wherein the second silica precursor has the general formula (II):

$$R^3_m\text{—Si—}(OR^4)_n \qquad (II)$$

wherein $R^3$ is selected from substituted and unsubstituted alkyl, substituted and unsubstituted aryl, alcohols, amines, amides, aldehydes, acids, esters, and functional groups having an unsaturated carbon-carbon bond, $R^4$ is an alkyl group, m+n=4, and m=0, 1, 2 or 3.

4. The method of claim 3 further comprising:
(d) adding a third silica precursor to the emulsion such that the third silica precursor can be emulsion templated on the droplets or deposited on the hollow silica-based particles to form hollow silica-based particles, wherein the third silica precursor has the general formula (III):

$$R^5_a\text{—Si—}(OR^6)_b \qquad (III)$$

wherein $R^5$ is selected from substituted and unsubstituted alkyl, substituted and unsubstituted aryl, alcohols, amines, amides, aldehydes, acids, esters, and functional groups having an unsaturated carbon-carbon bond, $R^6$ is an alkyl group, a+b=4, and a=0, 1, 2 or 3.

5. The method of claim 2 wherein:
the silica particle is modified from a continuously formed shell to a partially formed hollow shell by adjusting a ratio of the prehydrolyzed silica precursor and the second silica precursor in the emulsion.

6. The method of claim 2 wherein:
the prehydrolyzed silica precursor leaves a first shell thickness of 1 nanometer to 500 nanometers for the particle when the prehydrolyzed silica precursor and the second silica precursor are templated on a droplet, and the second silica precursor bonds to the first shell to create an outer layer such that the first shell and the outer layer together have a thickness in the range of 1 nanometer to 1 micron.

7. The method of claim 1 wherein:
step (a) further comprises adding a charged polymer to the emulsion, wherein the charged polymer is cationic.

8. The method of claim 1 wherein:
the $R^1$ groups are capable of attaching a coating by covalent bonding, non-covalent bonding, ionic bonding, electrostatic attraction, or any other attachment mechanism which allows for coating proximity within sub-nanometer ranges to 500 microns.

9. The method of claim 8 wherein:
the coating comprises a polymeric material.

10. The method of claim 1 wherein:
$R^1$ is phenyl.

11. The method of claim 1 wherein:
$R^1$ is $C_{12}$-$C_{24}$ alkyl.

12. The method of claim 1 wherein:
$R^1$ is substituted or unsubstituted acrylic acid.

13. The method of claim 1 wherein:
$R^1$ is polyethylene glycol.

14. The method of claim 1 wherein:
$R^1$ is alkylamine.

15. The method of claim 1 wherein:
$R^1$ is alkyl carboxylate.

16. The method of claim 1 wherein:
$R^1$ is alkyl quaternary amine.

17. The method of claim 1 wherein:
step (a) comprises adding a surfactant selected from cationic, anionic, nonionic and amphoteric surfactants to a first material comprising the continuous phase and a second material comprising the dispersed phase to form the emulsion.

18. The method of claim 1 wherein:
the emulsion templating is undertaken at a pH above 7.

* * * * *